(12) United States Patent
Cameron et al.

(10) Patent No.: US 10,512,472 B2
(45) Date of Patent: Dec. 24, 2019

(54) SURGICAL CUTTING INSTRUMENTS

(71) Applicant: DEPUY (IRELAND), County Cork (IE)

(72) Inventors: Rod G. Cameron, Franklin, MA (US); John Cuneo, Norton, MA (US); Michael J. Fortin, Acushnet, MA (US); Patnelli Richard, Leeds (GB)

(73) Assignee: DEPUY IRELAND UNLIMITED COMPANY (IE)

( * ) Notice: Subject to any disclaimer, the term of this patent is extended or adjusted under 35 U.S.C. 154(b) by 395 days.

(21) Appl. No.: 15/104,804

(22) PCT Filed: Dec. 16, 2014

(86) PCT No.: PCT/GB2014/053706
§ 371 (c)(1),
(2) Date: Jun. 15, 2016

(87) PCT Pub. No.: WO2015/092377
PCT Pub. Date: Jun. 25, 2015

(65) Prior Publication Data
US 2017/0014141 A1    Jan. 19, 2017

(30) Foreign Application Priority Data
Dec. 16, 2014  (GB) ................... 1322237.7

(51) Int. Cl.
*A61B 17/16*  (2006.01)
*A61F 2/46*  (2006.01)
(Continued)

(52) U.S. Cl.
CPC ...... *A61B 17/1617* (2013.01); *A61B 17/1642* (2013.01); *A61B 17/1666* (2013.01);
(Continued)

(58) Field of Classification Search
CPC combination set(s) only.
See application file for complete search history.

(56) References Cited

U.S. PATENT DOCUMENTS 4,023,572 A    5/1977  Weigand
4,662,891 A    5/1987  Noiles
(Continued)

FOREIGN PATENT DOCUMENTS

DE          2437772 A1    2/1976
DE    202010005376 U1    8/2010
(Continued)

*Primary Examiner* — Samuel S Hanna

(57) ABSTRACT

Surgical cutting instruments and methods of use are described. The surgical cutting instrument (100) comprises an instrument body (102) with a first attachment mechanism (106) at a distal end. A cutter (104) has a central core (110), a plurality of cutting formations (130, 136) and a plurality of lobes (112, 114, 116) extending from the central core. The central core has side walls (118, 120, 122) which define an entirely open mouth and the side walls include a second attachment mechanism (140, 142, 144) which can interact with the first attachment mechanism to releasably attach the cutter to the distal end of the instrument body. At least one cutting formation (136) is provided on an end outer face (138) of the cutter opposite the entirely open mouth.

12 Claims, 6 Drawing Sheets

(51) Int. Cl.
*A61F 2/34* (2006.01)
*A61F 2/40* (2006.01)
*A61F 2/30* (2006.01)

(52) U.S. Cl.
CPC ........ *A61B 17/1684* (2013.01); *A61F 2/4684* (2013.01); *A61B 2017/1602* (2013.01); *A61F 2/34* (2013.01); *A61F 2/4081* (2013.01); *A61F 2002/30426* (2013.01); *A61F 2002/30616* (2013.01)

(56) References Cited

U.S. PATENT DOCUMENTS

| | | | |
|---|---|---|---|
| 4,712,951 | A | 12/1987 | Brown |
| 4,802,468 | A | 2/1989 | Powlan |
| 5,116,165 | A | 5/1992 | Salyer |
| 5,295,992 | A | 3/1994 | Cameron |
| 5,302,234 | A | 4/1994 | Grace |
| 5,431,657 | A | 7/1995 | Rohr |
| 5,462,548 | A | 10/1995 | Pappas |
| 5,540,697 | A | 7/1996 | Rehmann |
| 5,584,837 | A | 12/1996 | Petersen |
| 5,817,096 | A | 10/1998 | Salyer |
| 5,879,355 | A | 3/1999 | Ullmark |
| 5,976,148 | A | 11/1999 | Charpenet |
| 6,015,411 | A | 1/2000 | Ohkoshi |
| 6,102,915 | A | 8/2000 | Bresler |
| 6,168,600 | B1 | 1/2001 | Grace |
| 6,221,076 | B1 | 4/2001 | Albrektsson |
| 6,409,732 | B1 | 6/2002 | Salyer |
| 6,730,094 | B2 | 5/2004 | Salyer |
| 6,875,217 | B2 | 4/2005 | Wolford |
| 7,118,575 | B2 | 10/2006 | Wolford |
| 7,220,264 | B1 | 5/2007 | Hershberger |
| 7,335,207 | B1 | 2/2008 | Smith |
| 7,621,921 | B2 | 11/2009 | Parker |
| 7,744,602 | B2 | 6/2010 | Teeny |
| 7,763,031 | B2 | 7/2010 | Tulkis |
| 8,123,815 | B2 | 2/2012 | Meridew |
| 8,308,810 | B2 | 11/2012 | Meridew |
| 8,357,163 | B2 | 1/2013 | Sidebotham |
| 8,435,243 | B2 | 5/2013 | White |
| 8,556,897 | B2 | 10/2013 | Sidebotham |
| 8,679,124 | B2 | 3/2014 | Lechot |
| 8,771,275 | B2 | 7/2014 | Xie |
| 8,870,886 | B2 | 10/2014 | Burgi |
| 9,439,781 | B2 | 9/2016 | Gibson |
| 2003/0050645 | A1 | 3/2003 | Parker |
| 2003/0130741 | A1 | 7/2003 | McMinn |
| 2004/0073224 | A1 | 4/2004 | Bauer |
| 2004/0073226 | A1 | 4/2004 | Cotting |
| 2004/0117029 | A1 | 6/2004 | Lewis |
| 2004/0133210 | A1 | 7/2004 | Wolford |
| 2005/0038443 | A1 | 2/2005 | Hedley |
| 2005/0085823 | A1 | 4/2005 | Murphy |
| 2005/0228394 | A1 | 10/2005 | Bihary |
| 2005/0261694 | A1 | 11/2005 | Orton |
| 2006/0025774 | A1 | 2/2006 | Fishbein |
| 2006/0079906 | A1 | 4/2006 | Timperley |
| 2006/0217730 | A1 | 9/2006 | Termanini |
| 2007/0203583 | A1 | 8/2007 | Slone |
| 2007/0233132 | A1 | 10/2007 | Valla |
| 2007/0276394 | A1* | 11/2007 | Johnson ............. A61B 17/1666 606/80 |
| 2008/0009952 | A1 | 1/2008 | Hodge |
| 2008/0195106 | A1 | 8/2008 | Lewis |
| 2008/0215159 | A1 | 9/2008 | Stamp |
| 2009/0088757 | A1 | 4/2009 | Tulkis |
| 2009/0163921 | A1 | 6/2009 | Lechot |
| 2010/0069908 | A1 | 3/2010 | Sidebotham |
| 2010/0145342 | A1 | 6/2010 | Grace |
| 2010/0168749 | A1 | 7/2010 | Sidebotham |
| 2010/0168752 | A1 | 7/2010 | Edwards |
| 2010/0186477 | A1 | 7/2010 | Barthelemy |
| 2010/0272533 | A1 | 10/2010 | Hecht |
| 2011/0202060 | A1 | 8/2011 | White |
| 2011/0208202 | A1 | 8/2011 | Zumsteg |
| 2011/0213372 | A1 | 9/2011 | Keefer |
| 2012/0185059 | A1 | 7/2012 | Vankoski |
| 2013/0131741 | A1 | 5/2013 | Kourtis |
| 2013/0211407 | A1 | 8/2013 | Geebelen |
| 2013/0267957 | A1 | 10/2013 | Stamp |
| 2013/0325139 | A1 | 12/2013 | Steiner |
| 2014/0114321 | A1 | 4/2014 | Davenport |
| 2014/0163564 | A1 | 6/2014 | Bollinger |
| 2014/0228854 | A1 | 8/2014 | Witt |
| 2014/0324183 | A1 | 10/2014 | Springer |
| 2015/0100060 | A1 | 4/2015 | Black |
| 2015/0366568 | A1 | 12/2015 | Victor |
| 2016/0089156 | A1 | 3/2016 | Fortin |
| 2016/0089158 | A1 | 3/2016 | Fortin |
| 2016/0175112 | A1 | 6/2016 | Pruvost |

FOREIGN PATENT DOCUMENTS

| | | |
|---|---|---|
| DE | 102011000976 A1 | 8/2012 |
| EP | 147339 A2 | 7/1985 |
| EP | 1183998 A2 | 3/2002 |
| JP | H05-29510 U | 4/1993 |
| JP | 2005522260 A | 7/2005 |
| JP | 2006288863 A | 10/2006 |
| RU | 1804314 C | 3/1993 |
| SU | 1568985 A1 | 6/1990 |
| WO | WO 2007121313 A2 | 10/2007 |

\* cited by examiner

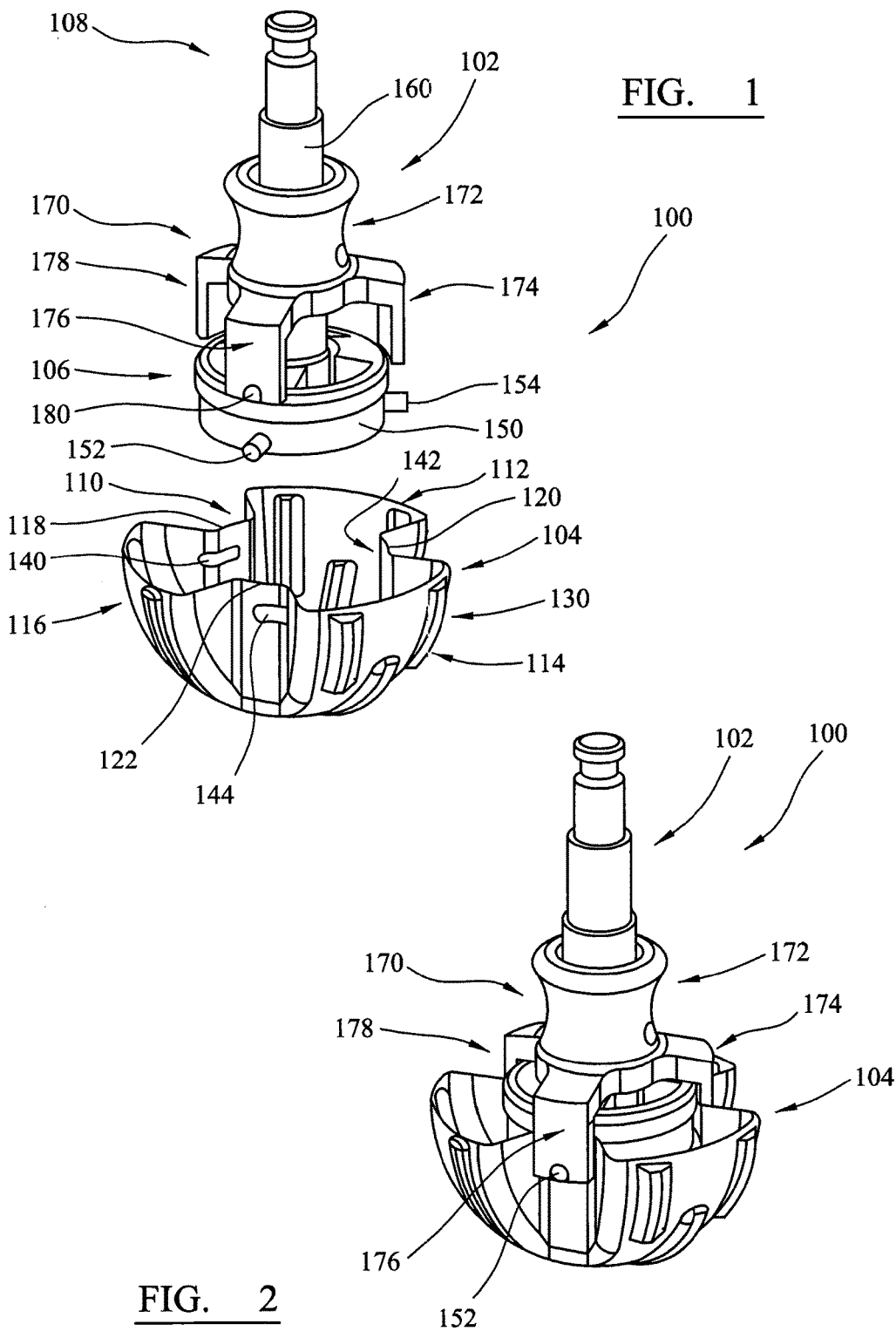

SURGICAL CUTTING INSTRUMENTS

CROSS REFERENCE TO RELATED PCT APPLICATION

This application is a National Stage 35 U.S.C. 371 of International Patent Application PCT/GB2014/053706filed Dec. 16, 2014, which claims priority to United Kingdom Application No. 1322237.7, filed Dec. 16, 2013, both of which are incorporated by reference in their entireties.

Orthopedic surgical procedures often involve the preparation of the patient's bone so that it can accept a component such as a prosthetic component. For example, one or more flat surfaces may be prepared on the tibia and/or fibula in order to accept one or more knee prostheses and the pelvis and/or femur may be prepared in order to accept one or more hip prosthetic components. Flat bone surfaces may also be prepared as an intermediate step in an orthopedic procedure.

When a surgical procedure relates to a ball and socket type joint, such as the shoulder or hip, then it can be necessary to prepare a cavity to accept a cup like prosthetic component to replace the bearing surface of the acetabulum or glenoid. Often a surgical reamer is used to prepare the cavity. A reamer instrument generally includes a rotating reamer bearing cutting formations, a body by which the surgeon can hold the instrument and a coupling to a source of rotational drive which is often a power tool, but can also be manual. Often, the reamer can be removed from the instrument so that a different sized reamer can be used, for example because of the size of the patient or in order to progressively increase the size of the cavity to match the size of a planned prosthetic implant. Hence, a releasable attachment mechanism is often provided to allow the reamer to be replaceably attached to the remainder of the reamer instrument so that different sized reamers can be used.

A known reamer attachment mechanism includes a pair of members arranged in a cross or X-shape and extending across the mouth of the reamer and to which the reamer instrument handle is attached by a kind of bayonet fitting, and is provided by the Greatbatch Inc. of Clarence, N.Y., USA. This provides a strong coupling to impart rotational drive to the reamer. However, it increases the complexity of manufacture of the reamer, increases its weight and increases the amount of material used to make the reamer. However, it does help to improve the mechanical strength of the reamer by acting as a brace between opposed sides of the reamer. The cross members also make it more difficult to clean the reamer for re-use.

U.S. 2004/0133210 describes an attachment mechanism for an acetabular reamer in which side wall portions of a hemi-spherical reamer within the concave interior of the reamer provide an attachment mechanism for a driver.

Calcar planers or mills are also generally known and can be used to remove hard calcar bone during an orthopedic procedure. These also tend to have either attachment features to which an instrument body can be attached or a permanently attached instrument body in order to impart rotational drive to the planer or mill. However, these increases the complexity of manufacture of the planer or mill, increases its weight and increases the amount of material used to make them. They can also make it more difficult to clean the reamer for re-use.

Therefore, it would be desirable to be able to provide a surgical cutting instrument having a simpler releasable attachment mechanism for a cutting part.

A first aspect of the invention provides a surgical cutting instrument comprising an instrument body having a distal end and a first attachment mechanism at the distal end; and a cutter having a central core, a plurality of cutting formations and a plurality of lobes extending from the central core. Each lobe can bear at least one cutting formation on an outer surface. Each outer surface can have a curved shape. The central core can have side walls which define an entirely open mouth. The side walls can include a second attachment mechanism which can interact with the first attachment mechanism to releasably attach the cutter to the distal end of the instrument body. At least one cutting formation can be provided on an end outer face of the cutter opposite the entirely open mouth.

By allowing the reamer body to attach to side walls of a central core of the cutter, no attachment members extending into or across the mouth of at least the core of the cutter need to be provided. This provides a simpler construction of the cutter. This also provides improved access to the interior cavity of the cutter during use. This provides a number of further advantages, such as improved visibility and also the ability more easily to collect material cut from the patient's bone. The open mouth also enables a trialling assembly and technique to be realised by allowing a trial component easily to be inserted into the cutter.

The cutter can have a side outer face and at least one cutting formation can be provided on the side outer face. Each lobe can provide a portion of the side outer face and/or a portion of the end outer face. Each side outer face can be curved. Each side outer face can be curved in a first and a second directions and/or may have the form or shape of a portion of the surface of a sphere, spheroid or three dimensional curved body. Each side outer face can provide at least one of the plurality of cutting formations.

The cutter can be arranged or configured to form a curved, concave cavity within a bone. The cutter can be a reamer suitable for a socket of a ball and socket type joint. The cutter can be an acetabular reamer or a glenoid reamer.

A plurality of cutting formations can be provided on the end outer face.

All of the plurality of cutting formations can be provided on the end outer face.

The end outer face can be at least partially or wholly substantially planar or flat.

The cutter can be arranged or configured to form a substantially planar or flat surface on a bone. The cutter can be a planer or mill.

Each lobe can bear a plurality of cutting formations. At least one or a plurality of cutting formations can be provided on a curved end surface of the cutter. The or each cutting formation can be a cutting slot.

Each lobe can be formed by a lobe wall. The lobe wall can provide the outer surface.

Each lobe wall can define a lobe mouth which is entirely open. Each lobe wall can include a first radial portion, a peripheral portion and/or a second radial portion. The peripheral portion can be curved.

The mouth of the core and the lobe mouths can be continuous or contiguous and can provide an entirely open mouth of the cutter.

The cutter can be formed from a single piece of material. The cutter can have an entirely unitary construction. The cutter can be made from a single piece of material. For example, the piece of material can be a sheet of material and in particular a sheet of metal. Suitable metals include steel and alloys of steel, such as stainless steel. The sheet of metal can have a thickness of less than 2 mm and in particular less than 1 mm, and more particularly less than 0.7 mm.

The second attachment mechanism can be located or positioned toward or adjacent the entirely open mouth of the cutter.

One of the first attachment mechanism and the second attachment mechanism can include one, at least one or a plurality of male formations and the other can comprise one, at least one or a plurality of female formations.

The second attachment mechanism can comprises one, at least one or a plurality of female formations. The or each female formation can be formed in the side walls of the central core. Each formation can be in the form of a slot. The slot can extend at least partially into a part of a lobe wall to provide an opening or entrance to the slot.

The first attachment mechanism can include a lock. The lock can be actuable to secure the cutter to the distal end. The lock can include one or more parts which act on an outer surface of the side walls of the central core.

The lock can include a locking member which can be translated along a longitudinal axis of the instrument body to change the lock from a locked configuration or state to an unlocked configuration or state. The locking member can interact with male members of the first attachment mechanism.

In the locked configuration a portion or part of the locking member can extend into a recess formed between an adjacent pair of lobes. This can prevent rotation of the cutter relative to the distal end of the instrument body.

The lock can include a biassing member arranged to bias the lock into the locked configuration. The biassing member can be a spring such as a coil spring.

The first attachment mechanism can include an engagement part or end dimensioned and shaped to extend between the side walls of the central core. The engagement part or end can be dimensioned and shaped to be received in and fill the mouth of the central core. The engagement part or end can have a circular periphery or have an at least partially circular periphery.

The cutter can include an intervening outer surface region located between each adjacent pair of lobes. The plurality of cutting formations can be provided on the plurality of lobes only and not on the intervening outer surface regions. The plurality of cutting formations can be provided on an end surface of the cutter also, but not on the intervening outer surface regions.

The cutter can have two, three or four lobes. The lobes can be equi-angularly spaced about a central axis of the cutter.

A second aspect of the invention provides a kit of parts comprising: the surgical cutting instrument of the first aspect of the invention; and a further cutter. The further cutter can have a central core and a plurality of lobes extending from the central core. The central cores of the further cutter and cutter can have the same lateral size. The lateral size can be a diameter when the central cores have a circular shape or form.

This provides a modular surgical cutting instrument in which different cutters can be used with the same instrument body as the parts of the cutter cores that attach to the instrument body have the same relevant size.

The cutter and further cutter can be different sizes. The cutter can be larger than the further cutter. The cutter can be smaller than the further cutter. A lateral dimension of the cutter and further cutter can be different. The lateral dimension can be a diameter when the cutter and further cutter each have a circular shape or form.

The distance between the outer surface of a lobe and a central rotational axis of the cutter can be different to the distance between the outer surface of a lobe and a central rotational axis of the further cutter.

The cutter and further cutter can be different types of cutter. For example, the cutter and further cutter can be selected from a reamer, a planer or mill.

The cutter and further cutter can be the same type of cutter.

The cutter and further cutter can each be a reamer.

The kit of parts can further comprise a trial liner. The trial liner can be dimensioned and shaped to be received within the central core of the reamer and the central core of the further reamer.

The trial liner can include a third attachment mechanism which can interact with the second attachment mechanism to control the depth of insertion of the trail liner into the central core.

The third attachment mechanism can comprises a plurality of male members which extend from an outer surface of the trial liner.

The plurality of male members comprises a first group of male members and a second group of male members. The first group of male members and the second group of male members can be at different positions along a longitudinal axis of the trial liner.

The trial liner can include a concave portion providing a trial cup for a ball and socket type joint. The concave portion can provide a trial articulating surface.

A third aspect of the invention provides a kit of parts comprising: the surgical cutting instrument of the first aspect of the invention and a trial liner. The cutter can be a reamer and the trial liner can be dimensioned and shaped to be received within the central core of the reamer.

This allows a trialling technique to be provided in which an assembly of the reamer and trial liner can more easily be assembled via the open mouth of the core of the reamer.

A fourth aspect of the invention provides a kit of parts comprising a reamer having a central core and a plurality of lobes extending from the central core. Each lobe can bear at least one cutting formation on an outer surface. Each outer surface can have a curved shape. The central core can have side walls which define a cavity and an entirely open mouth. The side walls can include a second attachment mechanism which can interact with a first attachment mechanism of an instrument body. The kit of parts further comprises a trial liner, wherein the trial liner is dimensioned and shaped to be received within the cavity of the central core of the reamer. The trial liner can have an articulating surface with a first lateral size. The articulating surface can be concave.

This allows a trialling technique to be provided in which an assembly of the reamer and trial liner can more easily be assembled via the open mouth of the core of the reamer.

The kit of parts can further comprise a further trial line. The further trial liner can be dimensioned and shaped to be received within the cavity of the central core of the reamer. The further trial liner can have an articulating surface with a second lateral size which is different to the first lateral size.

The kit of parts can further comprise a further reamer having a central core defining a cavity and a plurality of lobes extending from the central core. The trial liner can be dimensioned and shaped to be received within the cavity of the central core of the reamer.

The kit of parts can further comprise a further reamer having a central core defining a cavity and a plurality of lobes extending from the central core. The trial liner and further trial liner can be each dimensioned and shaped to be received within the cavity of the central core of the further reamer.

A fifth aspect of the invention comprises a method of assembling a surgical cutting instrument, comprising: introducing a first attachment mechanism of an instrument body into a cutter via an entirely open mouth of the cutter; and engaging the first attachment mechanism with a second attachment mechanism provided in a side wall of the cutter to releasably secure the instrument body to the cutter.

The method can further comprise rotating the instrument body and/or cutter relative to the other so as to engage the first attachment mechanism and the second attachment mechanism.

The method can further comprise actuating a lock to secure the instrument body to the reamer. The lock can engage an outer portion of the side wall of the cutter.

The method can also include counterpart method steps to the preferred features of any of the preceding aspects of the invention.

A sixth aspect of the invention provides a method of trialling a ball and socket type joint, comprising reaming a cavity using a reamer; and inserting a trial liner corresponding to a first cup size into the reamer.

The trial liner can be inserted into the reamer while the reamer is located within a reamed cavity in a bone of a patient.

The trial liner can be inserted into the reamer without removing the reamer from a reamed cavity in a bone of a patient.

The method can further comprise removing the trial liner from the reamer and inserting a further trial liner into the reamer. The second trial liner can correspond to a second cup size and the first cup size and second cup size can be different.

The method can further comprise further reaming the cavity using a further reamer having a different lateral size to the reamer and inserting the trial liner or a further trial liner into the further reamer.

The trial liner or further trial liner can be inserted into the further reamer while the further reamer is located within a reamed cavity in a bone of a patient.

The trial liner or further trial liner can be inserted into the further reamer without removing the further reamer from a reamed cavity in a bone of a patient.

A seventh aspect of the invention provides a method of reaming a cavity in a bone of a patient comprising at least partially reaming a cavity in a bone of a patient using a reamer having a totally open mouth; detaching an instrument body from the reamer; and removing bone graft material from the reamer via the totally open mouth of the reamer.

The bone graft material or harvested material can be removed from the reamer while the reamer is located in the at least partially reamed cavity in the bone of the patient.

An aspect of the invention provides a cutter having a central core and a plurality of lobes extending from the central core.

At least one cutting formation can be provided on an outer end face of the cutter. The outer end face can be opposite an entirely open mouth of the cutter.

Each lobe can bear at least one cutting formation on an outer surface. Each outer surface can have a curved shape. The central core can have side walls which define an entirely open mouth. The side walls can include a second attachment mechanism which can interact with the first attachment mechanism to releasably attach the reamer to the distal end of the instrument body.

Preferred features of the other aspects of the invention can also be preferred features of the reamer aspect of the invention.

Embodiments of the invention will now be described in detail, and by way of example only, with reference to the accompanying drawings, in which:

FIG. 1 shows a perspective view of a first embodiment of a surgical cutting instrument according to the invention in a disassembled state;

FIG. 2 shows a perspective view of the surgical cutting instrument shown in FIG. 1 in an assembled state;

Similar items in the different Figures share common reference signs unless indicated otherwise. Embodiments of the invention will now be described within the context of two example cutters; a reamer and a planer or mill. In particular an acetabular reamer will be described although it will be appreciated that the invention can also be applied to other types of reamers used to prepare curved cavities, such as glenoid reamers. It will be appreciated that glenoid reamers have a different size and shape to acetabular reamers and may include other parts to prepare a bore to receive a stem of a glenoid prosthesis. Also, in particular, a calcar planer or mill will be described. However, it will be apparent to a skilled person how to apply the specific teaching herein in relation to acetabular reamers to glenoid reamers and other rotationally symmetric reamers also, and the specific teaching herein in relation to calcar planers or mills to other rotational cutters more generally. Hence, the invention is not limited to acetabular reamers and/or calcar planers, but can be applied to other rotationally driven surgical cutters, both manual and powered.

In the following 'reamer' or 'reamer head' will generally be used to refer to the generally concave cutting part of the overall reamer instrument and 'instrument body' will be used to refer to a further or remaining part of the overall reamer instrument to which the reamer is releasably attached and which may also provide a coupling by which rotational drive can be communicated to the reamer.

Figure 3:
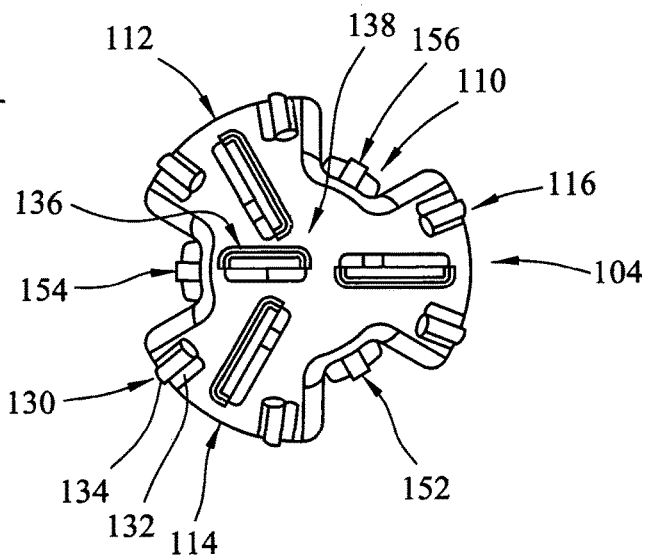
FIG. 3 shows a side view of the surgical cutting instrument shown in FIG. 2.
Figure 4:
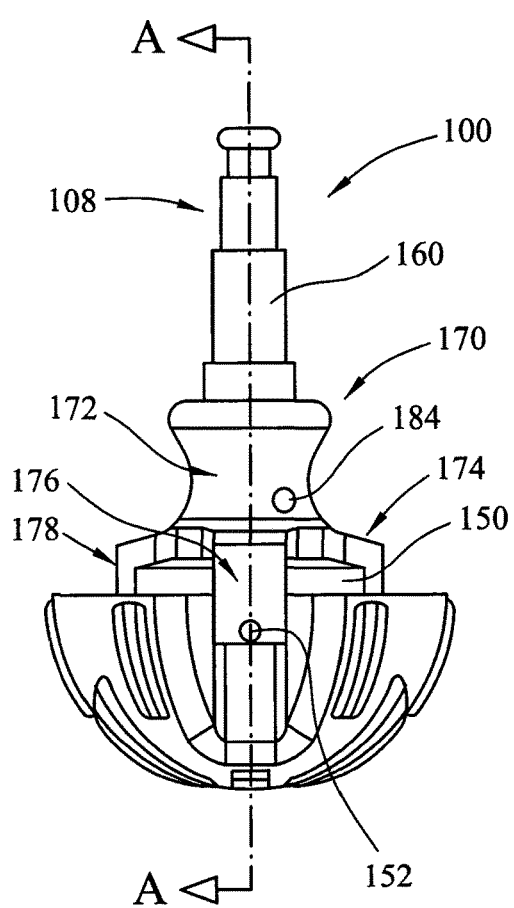
FIG. 4 shows a cross sectional side view of the surgical cutting instrument shown in FIG. 3.
Figure 5:
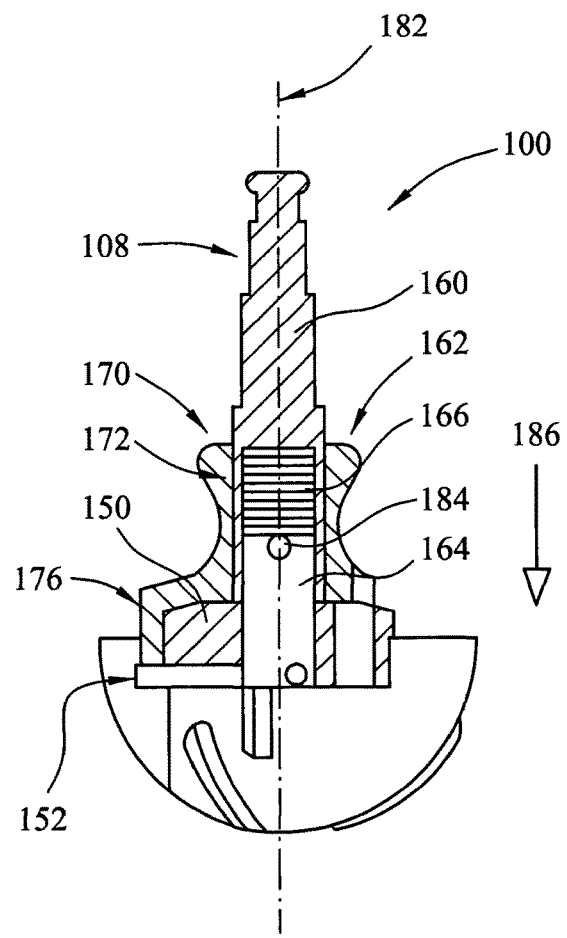
FIG. 5 shows an end view of the surgical cutting instrument shown in FIG. 2.

With reference to FIG. 1, there is shown a perspective view of a surgical cutting instrument 100 according to the invention. In FIG. 1, the instrument 100 is shown in a disassembled configuration. FIG. 2 also shows a perspective view of the instrument 100, but in an assembled configuration. The instrument 100 includes an instrument body 102 and a cutter in the form of a reamer 104. FIG. 3 shows an end view of the reamer instrument in which the reamer 104 is clearly visible. FIG. 4 shows a side elevation of the instrument 100 in the assembled configuration, and FIG. 5 shows a cross sectional view along line AA of the instrument 100 in its assembled configuration.

The instrument body 102 includes a first attachment mechanism 106 toward a distal end of the instrument body. A proximal end of the instrument body 102 includes a coupling formation 108 by which rotational drive can be applied, for example using a power tool or manual drive. In the illustrated embodiment, the coupling formation 108 is in the form of a Hudson coupling or end.

The reamer 104 includes a central circular core 110 and three lobes 112, 114, 116 extending from the central core. The central core 110 is defined by three sections of curved wall 118, 120, 122 each lying on the periphery of a circle centered on a central longitudinal axis of the instrument. The core 110 has an entirely open mouth.

Each lobe 112, 114, 116 is located between an adjacent pair of core wall segments. Each lobe is defined by a section of lobe wall, having a first portion extending in a generally radial direction, a second, curved portion, extending in a generally peripheral direction, and a third portion extending in a generally radial direction. The peripheral curved wall section of each lobe lies on the periphery of a circle, again centered on the central longitudinal axis of the instrument. An upper edge of each lobe wall defines a lobe mouth which is also entirely open. As illustrated in FIG. 1, the circular open mouth of the central core and the curved lobe mouths are continuous or contiguous and provide a single entirely open mouth of the reamer. Hence, there are no formations or members obstructing the entry to the reamer, or intruding into the interior cavity of the reamer, as is the case in prior art reamers in which cross members, and the like, are used as an attachment mechanism.

The curved walls of each lobe each bares a plurality of cutting formations, e.g. cutting formation 130. Each cutting formation comprises a slot and a wall structure about the slot including a cutting edge 134. Each cutting formation has a generally rectangular or slotted arrangement. However, it will be appreciated that other cutting formations and geometries can be used in practice. As illustrated in FIG. 3, cutting formations e.g. 140 are also provided on the outer surface of the curved underside or outer end face 138 of the reamer head and which is generally opposite the entirely open mouth.

The side walls 118, 120, 122 of the central core provide a second attachment mechanism which can interact with the first attachment mechanism 106 of the instrument body. Each core side wall 118, 120, 122 includes an elongate slot 140, 142, 144 extending in a generally peripheral direction and into a radial lobe wall portion.

The first attachment mechanism 106 includes a circular end member 150 having a diameter substantially matching the diameter of the central circular core 110. Circular end member 150 bares three pegs (only two of which 152, 154 are visible in FIG. 1). Each peg 152, 154, 156 extends in a generally radial direction and is sized to be accepted within corresponding peripheral slot 140, 142, 144 of the reamer 104. The circular end 150 is attached to a central circular cylindrical rod 160. As best illustrated in FIG. 5, a distal portion 162 of rod 160 defines a blind circular bore 164 in which a resilient member, e.g. a compressible spring 166, is located.

The first attachment mechanism 106 also includes a lock 170. The lock 170 has a generally annular body 172 with three legs 174, 176, 178 extending from a distal end thereof. A free end of each leg 174, 176, 178 includes a notch, e.g. notch 180. Each notch is shaped to receive the free end of a corresponding peg 152, 154, 156. The lock is slidably mounted about the rod 160 so that the lock can translate along the central longitudinal axis 182 of the reamer instrument. A pin 184 extends between opposed sides of the annular body 172 of the lock and passes through bore 164 of the rod 160. The pin 184 and spring 166 are arranged such that the spring 166 is compressed and biases the lock into a locked state by exerting a force in the generally distal direction as illustrated by arrow 186 in FIG. 5. The free end of each leg 174, 176, 178 is received in a respective recess formed between an adjacent pair of lobes. A part of each leg acts against a portion of an outer surface of the side walls forming the core. These act to clamp the side walls of the core to the distal end of the instrument to prevent them bowing outward under larger loads in use. This arrangement helps to stabilise or increase the rigidity or strength of the cutter. The outer surface of the lock body 172 has a generally concave shape to provide a grip for the fingers of a user of the instrument in use.

The first attachment mechanism, second attachment mechanism and lock thereby provide a lockable bayonet type releasable attachment mechanism by which the reamer can be releasably attached to the instrument body 102, but using the side walls of the reamer. Assembly and use of the reamer instrument will now be described. As mentioned above, FIG. 1 shows the instrument 100 in a disassembled state. A user can grasp the body 172 of the lock 170 using their fingers and pull the lock 172 in a generally proximal direction (the opposition of direction 186) along the longitudinal axis of the instrument 182 and against the action of spring 166. The instrument body is positioned generally concentrically with the central axis 182 of the instrument and with the pegs 152, 154, 156 extending into respective lobe portions of the reamer. The circular end member 150 is then inserted into the open mouth of the central core of the reamer. Then the instrument body and/or reamer are rotated relative to each other so as to engage pegs 152, 154, 156 into respective slots 140, 142, 144 via the open mouth portions of each slot extending into the lobe radial wall portions. Once the pegs 152, 154, 156 have been rotated into their respective slots 140, 142, 144, the user can release the lock 170. Spring 166 biases the lock in the generally distal direction 186 until the free end of each peg 152, 154, 156 is captured within a respective notch, e.g. 180, at the free end of each leg 174, 176, 178. This assembled configuration is illustrated in FIGS. 2 to 5.

As illustrated in FIGS. 2, 3 and 4 the width of each leg 174, 176, 178 substantially matches the width of each core wall section 120, 122, 124. Hence the legs 172, 174, 176 generally extend between adjacent lobe radial wall segments so as to prevent relative rotational movement between the instrument body and reamer. Also, the action of spring 166 biases the lock in the generally distal direction, toward the reamer, and therefore prevents the lock 170 from being released without application of unlocking force in the opposite direction.

The slots 140, 142 and 144 are located toward or adjacent the open mouth of the cutter. Hence, the distal end of the instrument body is also located at the open mouth of the cutter which also helps to increase the overall rigidity or stability of the cutter when assembled on the instrument body.

A drive tool, such as a powered drive tool or a manual drive, is then coupled to the drive coupling 108 and the reamer can then be introduced into the socket to be reamed. For example, if the reamer is an acetabular reamer, then the reamer can be introduced into the acetabulum of the patient in order to ream the acetabular cavity. In other embodiments, the reamer might be suitable for reaming other cavities, such as the glenoid cavity of the shoulder. The geometry of the reamer illustrated in the Figures is generally hemispherical and therefore suitable for an acetabular cavity. It will be appreciated that other reamer geometries are more appropriate for the glenoid which is shallower than the acetabulum.

The design of the general geometry, shape and size of a reamer suitable for reaming a glenoid cavity is considered to be apparent to a person of ordinary skill in the art from the teaching of this document.

During reaming, the reamer may be occasionally removed from the cavity in order to evaluate progress of the reaming. The drive tool and instrument body may be released from the reamer leaving the reamer in situ in the reamed or partially reamed cavity in the patient's bone so as to collect or harvest bone graft material from the interior of the reamer. At the end of the reaming process, the reamer instrument and attached drive tool may be entirely removed and the drive tool de-coupled from the coupling attachment 108. Additionally and/or alternatively, if further reaming is required to a different size, then a larger reamer may be attached to the instrument body. The modular nature of this part of the invention is described in further detail below.

In order to remove the reamer from the instrument body, the sequence of operations is generally reversed. A user grasps the lock 170 and applies a force in the generally proximal direction (opposition to direction 186). This disengages pegs 150, 152, 154 from respective notches in the legs 174, 176, 178 by translating the lock 170 along the longitudinal axis 182 of the instrument. Once the free ends of the legs are clear of the reamer, the instrument body and reamer can be rotated relative to each other to release pegs 152, 154, 156 from respective slots 140, 142, 144. The instrument body and reamer can then be separated by relative translation along the longitudinal axis 182 until circular end member 150 is free of the mouth of the central core 110.

As will be appreciated, the reamer of the invention has an entirely open mouth at least over the portion with which it engages the instrument body. This is in contrast to other reamer attachment mechanisms which often include members extending at least into if not across the mouth of the reamer. A number of advantages arise from attaching the reamer to the instrument body using the side walls of the reamer rather than using cross members or other parts extending into the mouth of the reamer and/or into the interior cavity of the reamer. Firstly, this provides improved visibility to surgeons in viewing the state of the reaming process. Further, it provides improved accessibility to the interior of the reamer. This can be particularly important when cut bone material is kept for other stages of the surgical procedure, such as retaining the cut bone for use as bone graft material or similar.

A number of other advantages arise from the configuration of the reamer as having a central core and plurality of lobes bearing cutting formations. As the outer surfaces of the walls of the core are recessed away from the cutting surface of the reamer, they do not bear cutting formations. This can improve the safety of handling of the reamer, and assembly and disassembly of the reamer instrument, as the walls of the central core provide a safe place for theatre staff to handle and manipulate the reamer, thereby reducing the risk of injury by the cutting formations.

A further advantage of the design of the reamer is that it is an entirely unitary construction that can more easily and simply be fabricated compared to previous reamers.

For example, in some embodiments, the reamer might be made using a 3D printing technique.

For example, in other embodiments, the reamer can be made from a single sheet of metal by using a pressing manufacturing technique. Some cutting steps may also be required in order to form the slots of the second attachment formation and also the cutting formations. Some further processing of the cutting formations to sharpen them may also be used. Suitable materials for the reamer include steels and alloys of steel, such as surgical grade stainless steels, including 17/4 PH Stainless Steel, and harder steels, such as grade 420 and 440B Stainless Steels.

Further advantages of the configuration of the reamer and entirely open mouth of the central core are further discussed below. In particular, the ability to use a single, or reduced number, of instrument bodies with reamers of different sizes, and also the ability to use the reamer as part of a trial assembly by introducing a trial liner into the central 30 core. Before discussing these further benefits of the invention, a further embodiment of the reamer instrument will be briefly described with reference to FIGS. 6 and 7.

Figure 6:
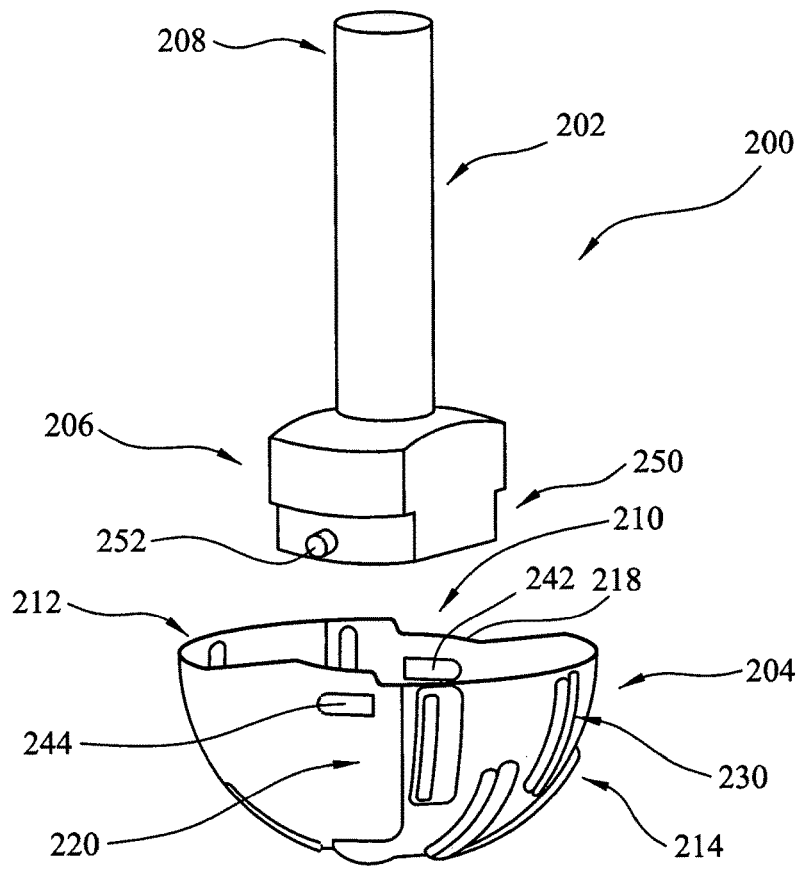
FIG. 6 shows a perspective view of a second embodiment of a surgical cutting instrument also according to the invention in a disassembled state.

With reference to FIG. 6 there is shown a second embodiment of a surgical cutting instrument 200 also according to the invention. Surgical cutting instrument 200 is generally similar to surgical cutting instrument 100 other than some of the details of the instrument body 202 and in that the cutter, in the form of reamer 204, includes two lobes 212, 214.

Figure 7:
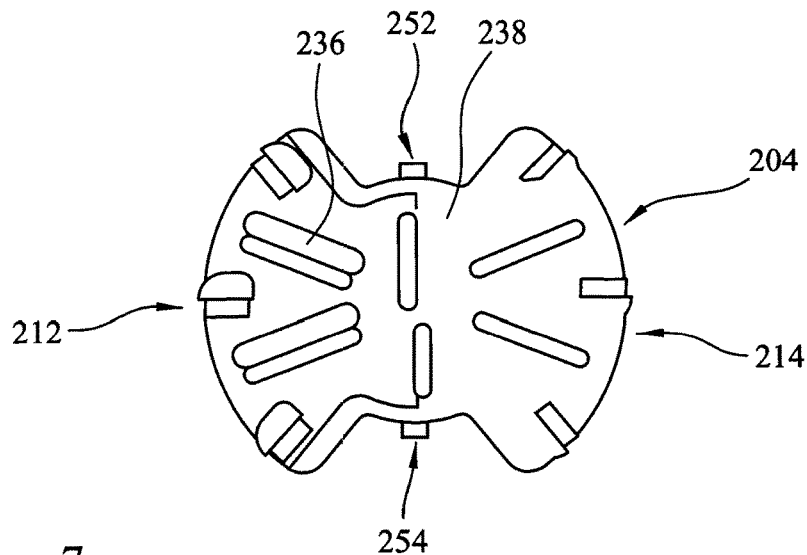
FIG. 7 shows an end view of the surgical cutting instrument shown in FIG. 6.

As in the first embodiment, the reamer 204 includes a generally circular core 210 defined by first and second opposed core walls 218, 220, each having a slot 242, 244 therein providing a second attachment mechanism. Each lobe 212, 214 is defined by a lobe wall having a first radial component, a second curved peripheral component, and a third generally radial component. The curved portion of each lobe wall bears a plurality of cutting formations, e.g. cutting formation 230, on an outer surface thereof. A plurality of cutting formations are also provided on the curved under or end surface of the reamer, e.g. cutting formation 236, as illustrated in FIG. 7. Again, as in the first embodiment, the second embodiment presents an entirely open mouth to the core, and also an entirely open mouth to each of the first and second lobes. The mouths of the core and lobes are continuous or contiguous and therefore the whole reamer has an entirely open mouth.

The instrument body 202 is generally similar to that of the first embodiment and also 20 includes a first attachment mechanism 206 at its distal end. A lock similar to that provided in the first embodiment can also be provided for the second embodiment but includes only a pair of legs rather than the three legs used in the first embodiment. The lock is omitted from FIGS. 6 and 7 for the sake of clarity or explanation only. Similarly to the first embodiment, the distal end of the instrument body provides a first attachment mechanism including a distal end portion 250 having two curved outer surface portions dimensioned to substantially match the inner diameter of the central circular core 210 of the reamer. A first 252 and a second 254 peg extend from opposed sides of the distal end part of the first attachment mechanism.

The first attachment mechanism and second attachment mechanism allow the distal end of an instrument body to be releasably attached to the reamer via a bayonet type mechanism in which the pegs 252, 254, can be twisted into the corresponding recesses 242, 244. As mentioned above, a lock mechanism similar to that described above in connection with the first embodiment can also be provided.

It will be appreciated that a greater number of lobes attached to a central core can also be provided in other embodiments. However, it is believed that beyond a fourth lobe, the spacing between the lobes may become insufficient and the performance of the reamer may be less good. The number of lobes to use is a balance between providing a curved cutting surface extending over a large portion of 360° while also reducing or managing any vibration possibly arising from the lobed structure of the reamer.

Some further benefits and advantages of the reamer aspect of the invention will now be described. In particular, the reamer aspect of the invention allows a modular approach to reaming instrumentation to be provided in which reamers of different sizes or diameters each have a core of the same size so that a single instrument body may be used with the different size reamers. Also, the entirely open mouth of the reamer core allows the reamer to be used as part of a trialling part of an orthopedic operation as described in greater detail below with referenced to FIGS. 9 to 13.

Generally, reamer instrument kits provide reamers with a plurality of different sizes either to accommodate patients of different sizes or to allow progressive reaming of the cavity. For example, reamers might be provided having a range of diameters from 38 mm up to 70 mm. As prior art reamers often include a cross member to provide coupling, there is no difficulty in attaching the reamer to the remainder of the reamer instrument as the cross members can be provided over the diameter of the different sized reamers. However, as the invention does not use members extending over or into the reamer cavity, a different approach is used to allow the same instrument body to be attached to reamers of different sizes. The general approach is illustrated in FIG. 8.

Figure 8:
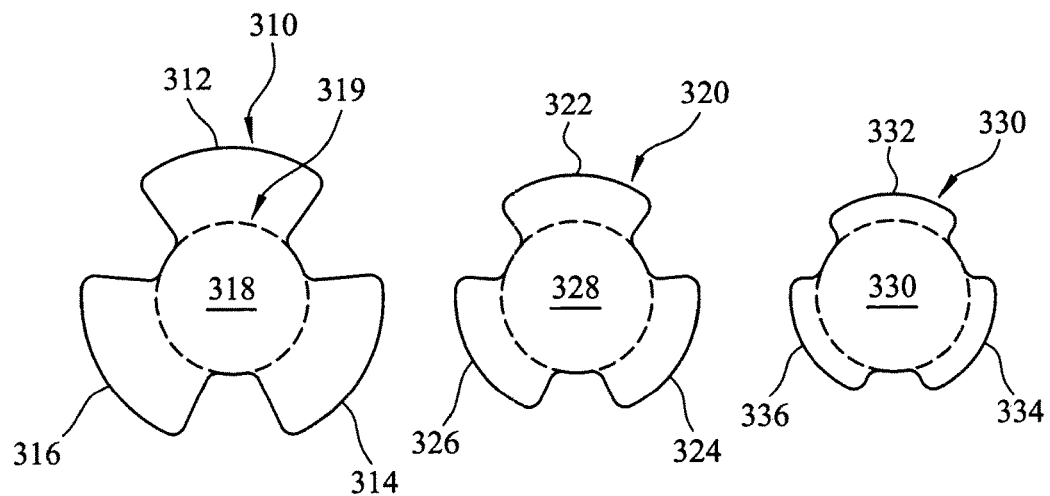
FIG. 8 shows a schematic plan view of a plurality of different sized reamers.

FIG. 8 shows schematic plan views of a first 310, second 320 and third 330 reamer according to the invention, and having decreasing sizes. That is, the first reamer 310 has the greatest diameter, the second reamer 320 has an intermediate diameter and the third reamer 330 has the smallest diameter. It will be appreciated that in practice, a greater or lesser number of reamers may be provided and three are illustrated here merely by way of simplicity of explanation. As used herein, diameter and the "size" of the reamer generally refers to the diameter of the circle on the periphery of which the curved walls of the lobes, e.g. curved walls 312, 314, 316, lie. As also illustrated in FIG. 8, each reamer 310, 320, 330 includes a central core 318, 328, 338 defined by curved core wall portions as described above. Each core 318, 328, 330 of the different sized reamers has the same size. As illustrated in FIG. 8, the core walls fall on the periphery of a circle, illustrated in dashed lines in FIG. 8 having the same diameter. For example, in FIG. 8, circle 319 may have a diameter of approximately 30 mm. Hence, as the different sized reamers 310, 320, 330 each have the same sized core, 318, 328, 330, the equivalent body having the same sized attachment mechanism can be attached to any of the reamers. Hence, by providing a plurality of different sized reamers with a constant sized core, the potential problem caused by omitting cross members as an attachment mechanism is overcome by the constant sized core feature. This therefore allows retention of the entirely open mouth of the core, and also the lobes, which provides the benefits described above, in terms of visibility and bone graft material harvesting.

Hence, as described above, a reaming instrumentation kit may be provided with a single instrument body and multiple different sized reamers and the surgeon may select a reamer suitable for the patient from the provided reamers and only a single size of instrument body may be provided. Additionally or alternatively, the surgeon may select to use a different sized reamer intraoperatively after initially reaming with a smaller reamer and hence the surgeon can easily simply remove the smaller reamer from the instrument body and attach a larger reamer to the same instrument body.

It will be appreciated that in other embodiments, the reaming instrumentation may include a first plurality of different sized reamers each having a first commonly sized core. A further plurality of other different sized reamers may also be provided each having a constant sized core, but either greater or smaller in size to that of the first plurality. For example, this may be useful where a greater range of reamer sizes needs to be provided, for example to include a very small diameter reamer. For example, it may be desirable to provide smaller reamer sizes, for example from 24 mm up to 36 mm diameter. The smaller range of the reamers may therefore have a smaller core diameter, e.g. 20 mm, and then a second subset of larger reamers may have a larger core diameter, e.g. 34 mm. Hence, in this approach, two different sized instrument bodies would be used, a first having a 20 mm diameter attachment mechanism and the second having a 34 mm diameter attachment mechanism. Other variations will be apparent to the skilled person.

A trialling feature of the invention will now be described in greater detail with reference to FIGS. 9 to 13. As described above, the core has an entirely open mouth which provides easy access to the interior cavity of the reamer. Also, the interior cavity of the reamer has no formations or structures protruding into it. Hence, after reaming has been completed, the reamer may be left in situ in the reamed cavity and then a liner component may be introduced into the cavity of the reamer to serve as a cup trial component during a trialling stage of the orthopedic procedure.

Figure 9:
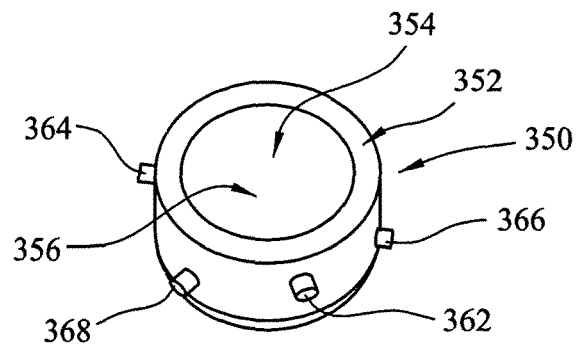
FIG. 9 shows a perspective view of a liner component used in an assembly according to the invention.
Figure 10:
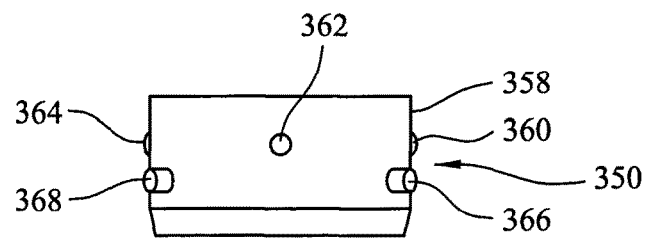
FIG. 10 shows a side view of the liner component shown in FIG. 9.

FIG. 9 shows a perspective view of a trial liner component 350. FIG. 10 shows a side elevation of the trial liner component 350. As illustrated in FIG. 9, the trial liner component 350 has a generally circular cylindrical shape with a diameter substantially matching the diameter of the central core of the reamer, e.g. 30 mm. An upper face 351 defines a concave recess or cavity 354 having a curved trial articulating surface 356. In an acetabular embodiment of the invention, the concave recess may have a hemispherical or part of a sphere shape. However, for a glenoid embodiment of the invention, a different curved surface shape for the concave cavity may be provided. As best illustrated in FIG. 10, a plurality of pegs extend in a generally lateral direction from an outer surface of a side wall 358 of the trial component 350. The plurality of pegs comprise a first sub-group of three pegs 360, 362, 364 and a second sub group of three pegs 366, 368 and the third of which is not visible in FIGS. 9 to 12. The first group of three pegs and the second group of three pegs are at different positions along a longitudinal axis of the trial component 350 so as to allow adjustment of the depth of insertion of the trial component into the reamer.

Figure 11:
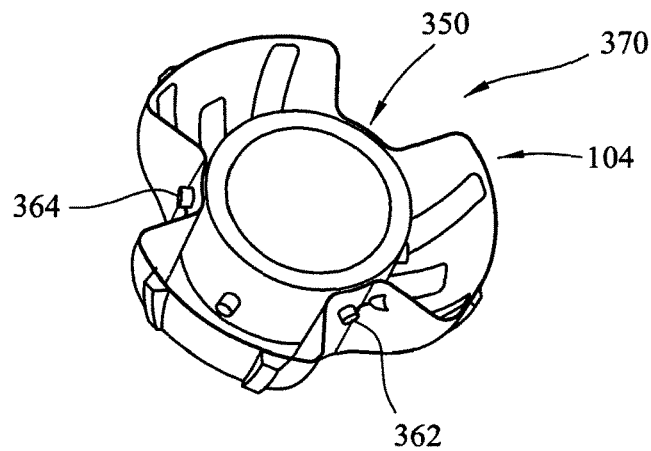
FIG. 11 shows a perspective view of an assembly of the reamer and a trial liner component in a first configuration according to the invention.

FIG. 11 shows a perspective view of an assembly 370 of the reamer 104 and trial liner 350 during a trialling stage of the orthopedic surgical procedure. The reamer 104 is either left in situ or placed within the reamed acetabular cavity and the trial liner component 350 is introduced into the cavity of the central core. Similarly to the bayonet fitting arrangement of the instrument body, the group of three pegs 360, 362, 364 provide an attachment mechanism which can interact with the second attachment mechanism of the reamer. That is, the three pegs 360, 362, 364 of the trial liner are engaged with the slots 140, 142, 144 and the trial liner twisted into position to lock to the reamer. The surgeon may then reduce the joint using a trial femoral component in order to evaluate the joint.

Figure 12:
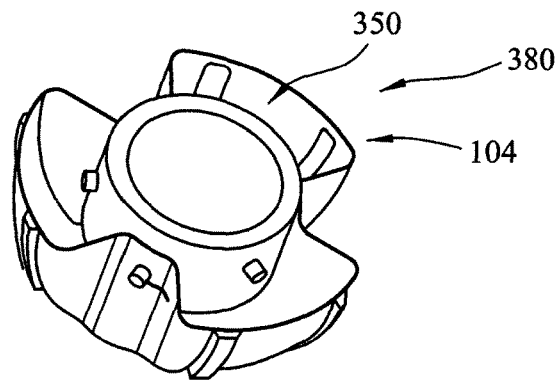
FIG. 12 shows a perspective view of the assembly of FIG. 11 in a second configuration.

The second set of pegs 366, 368 allows control of the depth of insertion of the trial liner into the reamer 104, as illustrated in FIG. 12. FIG. 12 shows a perspective view of a trial assembly comprising the reamer 104 and the trial liner component 350 but at a different depth of insertion compared to the trial assembly illustrated in FIG. 11. In FIG. 12, pegs 366, 368 and the third of the second set of pegs are engaged in the slots 140, 142, 144 of the reamer 104 and therefore limit the depth of insertion of the trial liner 350 into the central core cavity of the reamer 104. Hence, the trial assembly and procedure allows the lateralisation of the hip joint to be adjusted during the trialling procedure. The correct lateralisation of the hip joint can be an important factor in the stability of the hip joint.

The trial liner 350 is preferably made of a plastic or polymer material, in particular an Engineering plastic of polymer, such as Acetal, and the pins or pegs can be made from a surgical grade metal or alloy, such as stainless steel of a suitable grade, such as 17/4 PH, 316, 420 or 440.

Figure 13:
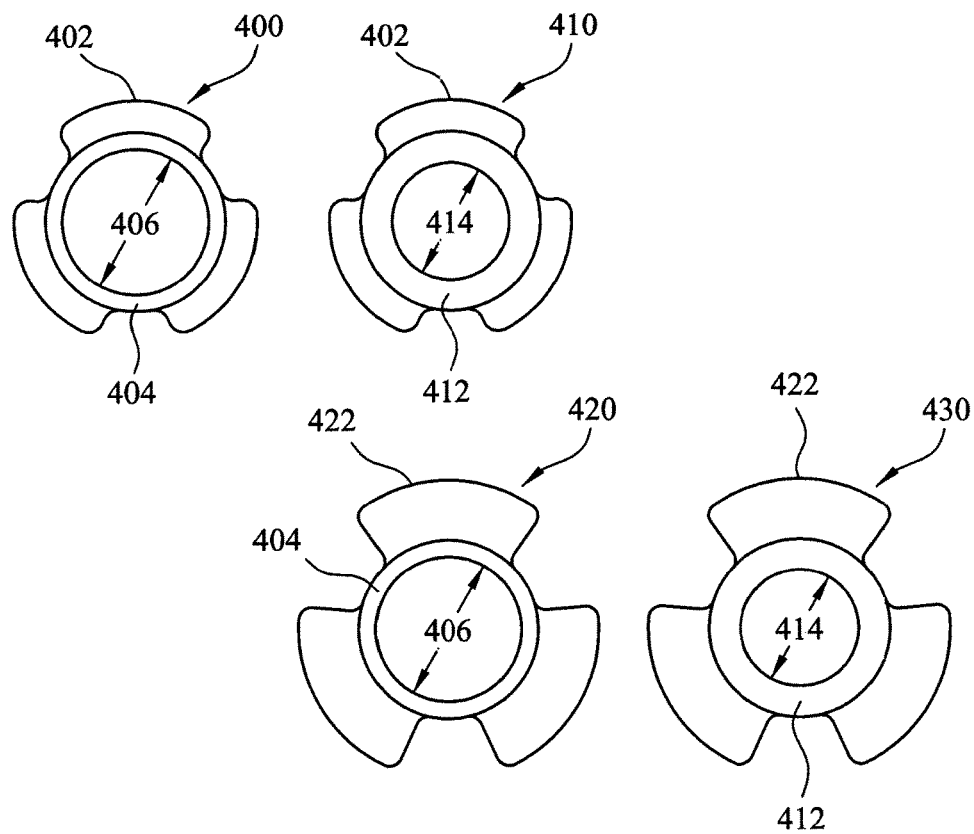
FIG. 13 shows a schematic plan view of a plurality of assemblies illustrating the use of different sized trial liner components with different sized reamers.

As will be appreciated, during trialling, the surgeon is attempting to determine the best size and positioning of the joint components. Therefore, in some instances, the surgeon may want to try different size femoral heads and therefore will want to be able to try trial liners corresponding to different sized cups. Hence, the trial instrumentation may include trial liners having the same outer diameter, corresponding to that of the central core, but having different diameter cavities therein, corresponding to different cup and head sizes. This modular aspect of the reamers and trialling liner is illustrated schematically in FIG. 13. For example, FIG. 13 shows a first trial assembly 400 comprising a reamer 402 and a first trial liner 404 corresponding to a first cup diameter 406. The instrumentation includes further trial liners having the same outer diameter but having a different size inner diameter. For example, trial assembly 410 comprises reamer 402 again. However, trial assembly 410 includes a second trial liner 412 having a lesser diameter 414 cavity corresponding to a smaller femoral head.

FIG. 13 also illustrates the modularity of the different trial liner sizes and different reamer sizes. For example, trial assembly 420 comprises reamer 422, having a greater diameter than reamer 402 of trial assembly 400, and trial liner 404 having a cup diameter 306. Hence, in the situation where the surgeon initially reams the cavity using reamer 402 and then trials using trial liner 404, the surgeon may subsequently further ream the cavity using larger reamer 422 and then re-trial using the same trial liner 404. FIG. 13 also shows a further trial assembly 430 comprising reamer 422 and trial 412 having a lesser diameter cup size 414 compared to trial liner 404. Hence, after trialling with cup size 406, a surgeon may determine that a smaller head may be more appropriate and may therefore trial with liner 412 having a lesser diameter 414. As each of the trials has the same outer diameter, and each of the different sized reamer has the same size core, improved modularity is provided in terms of the number of trial liners and reamers to provide a full range of trialling for different sized acetabular cups and femoral heads.

A further embodiment of the surgical cutting instrument of the invention will now be described with particular reference to FIGS. 14 and 15. In this further embodiment, the cutter has a different form to the cutter of the preceding embodiments and in particular is in the form of a planer or mill and in particular a calcar planer suitable for removing calcar bone when forming a flat surface on a bone. The instrument body part of the surgical cutting instrument has the same general form as that described above with reference to FIGS. 1 to 5. Hence, the invention also provides a modular approach to surgical cutting in which different cutters can be used with the same common instrument body owing to the common attachment arrangement between the cutters and distal end of the instrument body.

Figure 14:
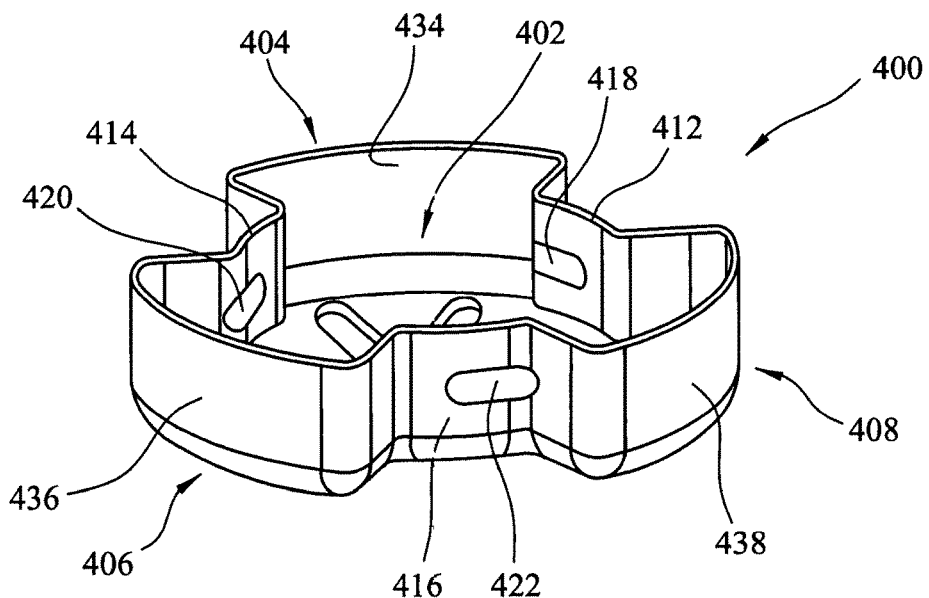
FIG. 14 shows a perspective view from a top side of a cutter of a surgical cutting instrument according to a further embodiment of the invention.

FIG. 14 shows a perspective view from a top side of a cutter 400 of a surgical cutting instrument according to a further embodiment of the invention. FIG. 15 shows a perspective view from an underside of the cutter 400. The cutter 400 is in the form of a calcar planer or mill and is suitable for forming a substantially flat or planar surface on a bone. The calcar planer 400 has a central core 402 and first 404, second 406 and third 408 lobes extending therefrom. Viewed in plan, the cutter 400 has a generally clover leaf configuration. The central core 402 is defined by side walls 412, 414, 416 each having a respective slot 418, 420, 422 therein and located toward or adjacent an entirely open end face of the calcar planer 400. The slots 418, 420, 422 provide the second attachment mechanism with which the pins or pegs of the first attachment mechanism of the instrument body can interact in order to releasably attach the cutter 400 to the instrument body. The diameter of the central core 402 is the same as that of central cores of the reamer embodiments of the cutter, and similar to that of the distal end of the instrument body, so that the same instrument body can be interchangeably used with either the reamer or the calcar planer as the cutter.

Figure 15:
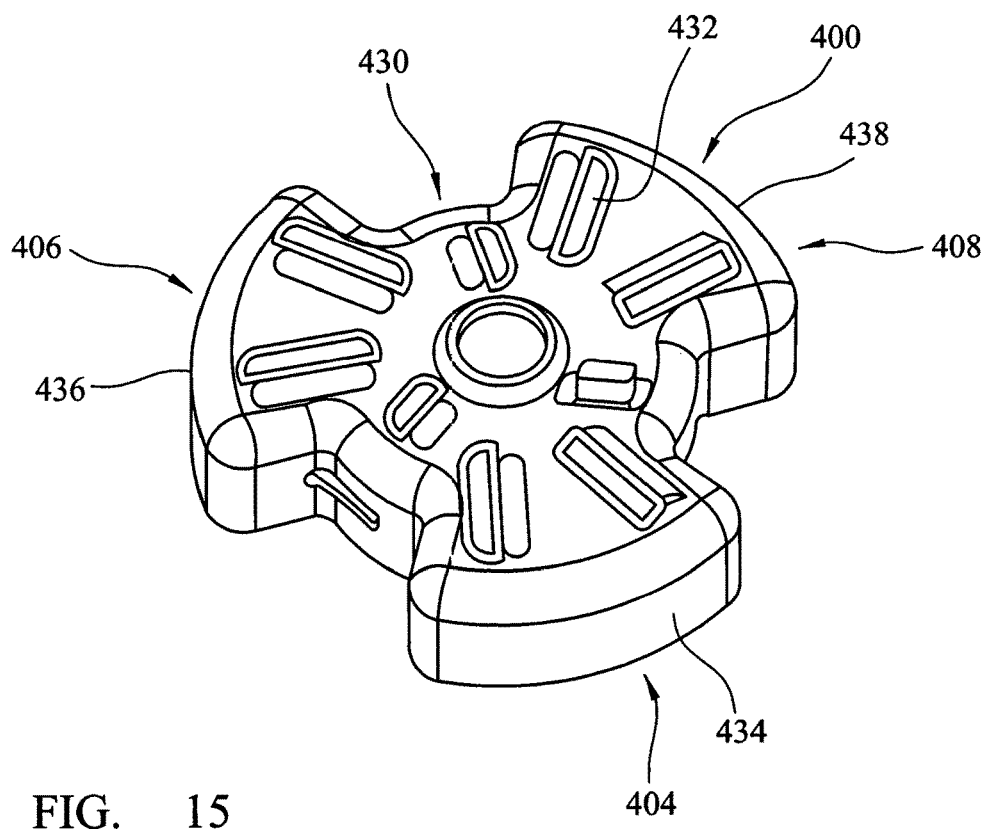
FIG. 15 shows a perspective view from an underside of the cutter illustrated in FIG. 14.

As best illustrated in FIG. 15, an end outer face 430 of the cutter 400 which is opposite the entirely open mouth bears a plurality of cutting formations, e.g. cutting formation 432, each in the form of a cutting slot. In the illustrated embodiment, there are three cutting formations located on a portion of the end outer face corresponding to the central core and two cutting formations on each respective portion of the end outer face corresponding to respective ones of the lobes 404, 406, 408. However, there are no cutting formations provided on lobe side wall portions 434, 436, 438 as the calcar planer is arranged to provide a planing or milling action to produce a substantially flat or planar bone surface.

The entirely open mouth of the calcar planer has a number of advantages similar to those of the reamer. It provides increased visual and physical access to the interior of the calcar planer, e.g. to remove bone fragments, and can also make it easier to clean for re-use.

Similarly to the design of the reamer cutter, the calcar planer cutter has an entirely unitary construction that can more easily and simply be fabricated compared to other cutters.

For example, in some embodiments, the calcar planer might be made using a 3D printing technique.

For example, in other embodiments, the calcar planer 400 can be made from a single sheet of metal by using a pressing manufacturing technique. Some cutting steps may also be required in order to form the slots of the second attachment formation and also the cutting formations. Some further processing of the cutting formations to sharpen them may also be used. Suitable materials for the calcar planer include steels and alloys of steel, such as surgical grade stainless steels, including 17/4 PH Stainless Steel, and harder steels, such as grade 420 and 440B Stainless Steels.

In some embodiments, a reasonably thin sheet of metal may be used to facilitate the pressing or forming of the cutter. For example, the cutter can be made from a sheet of 420 stainless steel having a thickness of about 0.635 mm to improve the ease of pressing or otherwise forming the cutter. However, the resulting cutter can then be less rigid particularly because of its open mouth. Hence, the attachment mechanisms are positioned toward or adjacent the open mouth so that the distal end of the instrument body, when received in the central core, can help to reinforce, stabilise or otherwise strengthen the cutter. Further, by providing parts of the lock which engage the outer surfaces of the core side walls these can help to resist any outward bowing forces in use which might otherwise distort the cutter.

As noted above, the common attachment interface between the different types of cutters and the instrument body means that the same instrument body can be used with multiple different types of cutters. Hence, the same instrument body can be used with the calcar planer at one stage of an orthopedic procedure, e.g. removing calcar bone from a resected distal part of the femur, and also at another stage of the orthopedic procedure, e.g. reaming an acetabular cavity. Hence, the amount of instrumentation used during a surgical procedure can be reduced.

Various changes and modifications to the specific embodiments described above will be apparent to a person of ordinary skill in the art from the teaching contained herein.

The invention claimed is:

1. A surgical cutting instrument comprising:
an instrument body having a shaft extending along a longitudinal axis from a proximal end to a distal end and a first attachment mechanism coupled to the shaft, wherein the first attachment mechanism includes an enlarged circular end member having a plurality of pegs projecting radially outward therefrom and coupled to the distal end of the shaft, the first attachment mechanism further includes a lock having an annular hollow body with a plurality of legs projecting radially outward and distally therefrom, wherein the hollow annular body is coaxially and slidably coupled to the shaft; and
a hemispherical cutter having a circular central core, a plurality of cutting formations and a plurality of outer lobes having a first radius convex lobes extending from a longitudinal axis of the central core and a plurality of inner concave lobes having a second radius from the longitudinal axis of the central core that is less than the first radius, wherein each of the outer lobes has a convex outer surface and a concave inner surface, and each of the inner lobes has a concave outer surface and a convex inner surface, the circular central core having side walls which define a continuous opening and the side walls including a second attachment mechanism configured to interact with the first attachment mechanism to releasably attach the cutter to the distal end of the instrument body and wherein the outer and inner surfaces of the plurality of outer and inner lobes are outer and inner surfaces of the side walls and wherein at least one cutting formation of the plurality of cutting formations is provided on an end outer face of the side walls of the cutter opposite the continuous opening; wherein the second attachment mechanism includes a plurality of slots extending through the plurality of inner concave lobes, each of the plurality of slots adapted to engage one of the plurality of pegs such that when the instrument body is inserted into the continuous opening of the cutter, the circular end member fits within the second radius and engages the inner surfaces of the plurality of the inner concave lobes and each of the pegs extend through a corresponding one of the slots, and the lock slides distally along the shaft to a locked configuration, such that each of the plurality of legs engages a corresponding one of the outer surfaces of one of the plurality of inner concave lobes and fits in an outer recess formed between adjacent two of the plurality of outer lobes, and such that each of the pegs engages a notch defined in a corresponding one of the plurality of legs to rotationally lock the instrument body with the hemispherical cutter.

2. The surgical cutting instrument as claimed in claim 1, wherein at least one of the plurality of cutting formations is provided on a side outer face of the side walls.

3. The surgical cutting instrument as claimed in claim 2, wherein each of the plurality of outer lobes provides a portion of the side outer face, and wherein each portion of the side outer face is curved and provides at least one of the plurality of cutting formations.

4. The surgical cutting instrument as claimed of claim 1, wherein the hemispherical cutter is arranged to form a curved, concave cavity within a bone.

5. The surgical cutting instrument as claimed in claim 4, wherein the hemispherical cutter is a reamer.

6. The surgical cutting instrument as claimed in claim 1, wherein the at least one cutting formation provided at the end outer face comprises a plurality of cutting formations provided on the end outer face.

7. The surgical cutting instrument of claim 1, wherein the hemispherical cutter is formed from a single piece of material.

8. The surgical cutting instrument of claim 7, wherein the single piece of material is a sheet of metal.

9. The surgical cutting instrument of claim 1, wherein the second attachment mechanism is located adjacent the entirely open mouth.

10. The surgical cutting instrument as claimed in claim 1, wherein the lock is configured to slide proximally along the shaft to change the lock from the locked configuration to an unlocked configuration.

11. The surgical cutting instrument of claim 1, wherein the plurality of cutting formations are provided on the plurality of outer lobes only and not on the plurality of inner concave lobes.

12. The surgical cutting instrument of claim 1, wherein the plurality of outer lobes being three outer lobes and wherein the plurality of outer lobes are equi-angularly spaced about the longitudinal axis of the central core of the hemispherical cutter.

* * * * *